United States Patent [19]

Shanks

[11] 4,377,089
[45] Mar. 22, 1983

[54] COMPRESSION TEST APPARATUS

[76] Inventor: Alan M. Lovelace, Administrator of the National Aeronautics and Space Administration, with respect to an invention of George C. Shanks, Malibu, Calif.

[21] Appl. No.: 234,223

[22] Filed: Feb. 13, 1981

[51] Int. Cl.³ ............................................. G01N 3/08
[52] U.S. Cl. ...................................................... 73/818
[58] Field of Search ................. 73/818, 821, 822, 823, 73/825, 790, 813; 177/146

[56] References Cited

U.S. PATENT DOCUMENTS 2,333,313  11/1943  Henderson ............................. 73/818
3,887,022  6/1975  Staner .................................. 177/146

*Primary Examiner*—Jerry W. Myracle
*Attorney, Agent, or Firm*—Russell E. Schlorff; John R. Manning; Marvin F. Matthews

[57] ABSTRACT

Apparatus for compressive testing of a test specimen may comprise vertically spaced upper and lower platen members (1 and 2) between which a test specimen (T) may be placed. The platen members are supported by a fixed support assembly (3, 5, and 6). A load indicator (14) is interposed between the upper platen member (1) and the support assembly (6) for supporting the total weight of the upper platen member (1) and any additional weight which may be placed thereon. Operating elements (8 and 17) are provided for moving the lower platen member (2) upwardly toward the upper platen member (1) whereby an increasing portion of the total weight is transferred from the load indicator (14) to the test specimen (T).

The testing apparatus may include limit devices (20 and 22) for limiting the movement of the lower platen member (2) toward the upper platen member (1) to prevent permanent deformation in the test specimen (T). In one embodiment, the limit devices include a plurality of rods (20) attached to one of the platen members (2) and a vertically adjustable extension member (22) engageable with the other platen member (1).

9 Claims, 2 Drawing Figures

COMPRESSION TEST APPARATUS

ORIGIN OF THE INVENTION

The invention described herein was made in the performance of work under a NASA Contract, and is subject to to provisions of Section 305 of the National Aeronautics and Space Act of 1958, Public Law 85-568 (72 Stat. 435; 42 U.S.C. 2457).

TECHNICAL FIELD

The present invention pertains to testing apparatus for testing the compressive characteristics of test specimens. In particular, it pertains to apparatus suitable for testing specimens of large, light-weight columns under axial compressive loading.

BACKGROUND ART

There are a number of testing fixtures or devices for determining compressive characteristics of materials. Many of these test fixtures are primarily designed for testing to failure concrete or other paving mixtures. Examples of such may be seen in U.S. Pat. Nos. 2,471,227; 2,447,586; and 2,637,198. There are, of course, testing fixtures used for other materials. U.S. Pat. No. 1,931,925 discloses an apparatus for testing fibers and U.S. Pat. No. 2,041,869 discloses apparatus for testing pharmaceutical tablets.

In compression test fixtures such as those mentioned above, the test specimen is commonly placed between vertically spaced platens which, as the test proceeds, are forced toward each other so as to apply increasing compressive forces to the test specimen. Some type of load indicator device is utilized for measuring the forces to which the specimen is subjected. In most of these devices, one of the platens is essentially fixed and the other is movable toward the fixed platen by some source of power. Frequently, such testing results in total destruction or permanent damage to the test specimen. Thus, the test specimen is no longer useful after testing.

DISCLOSURE OF THE INVENTION

In the present invention, a compressive testing fixture is provided with vertically spaced upper and lower platens between which a test specimen may be placed. The platen members are supported by a fixed support base. A load indicating device is interposed between the upper platen and the support base to initially support the entire weight of the upper platen and any additional weights placed thereon. The upper platen is therefore gravity loaded. Means are provided for moving the lower platen upwardly toward the upper platen whereby an increasing portion of the total weight on the upper platen is transferred from the load indicator to the test specimen. This feature of the present invention appears to be unique in that instead of lowering a platen weight on the test specimen, the specimen is used to raise the upper platen.

The test fixture of the present invention includes limit devices attached to one of the platens and engageable with the other to limit the movement of the lower platen toward the upper platen. The limit devices are adjustable for predetermining such limited movement so that although the specimen can be loaded to the buckling point, permanent deformation or damage may be prevented thereto. Thus, the test specimens can be used for further testing or actual use. This results in cost saving, particularly when the test specimen is of expensive materials or manufacture. Other advantages of the invention will be apparent from reading the description which follows in conjunction with the accompanying drawings.

DESCRIPTION OF A PREFERRED EMBODIMENT

Figure 1:
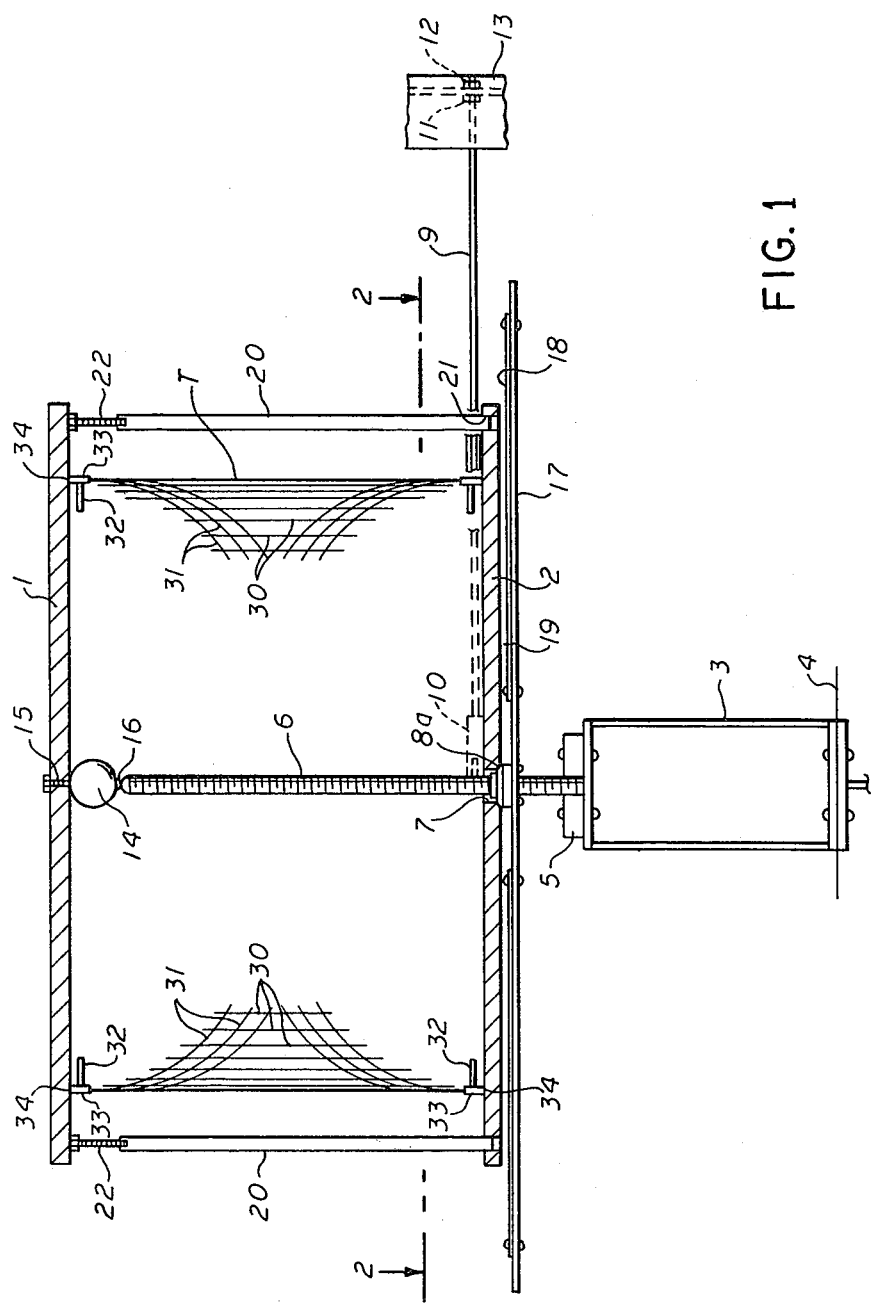
FIG. 1 is an elevation view of the compression testing apparatus of the present invention, partially in section, according to a preferred embodiment thereof.

Referring now to the drawings, the apparatus of the present invention includes upper and lower platen members 1 and 2, respectively, between which a test specimen T may be placed. The test specimen T illustrated in the drawing represents a large, lightweight column which may be utilized, for example, in composite structures for space construction. Of course, other types of specimens can be tested with the apparatus of the present invention.

Figure 2:
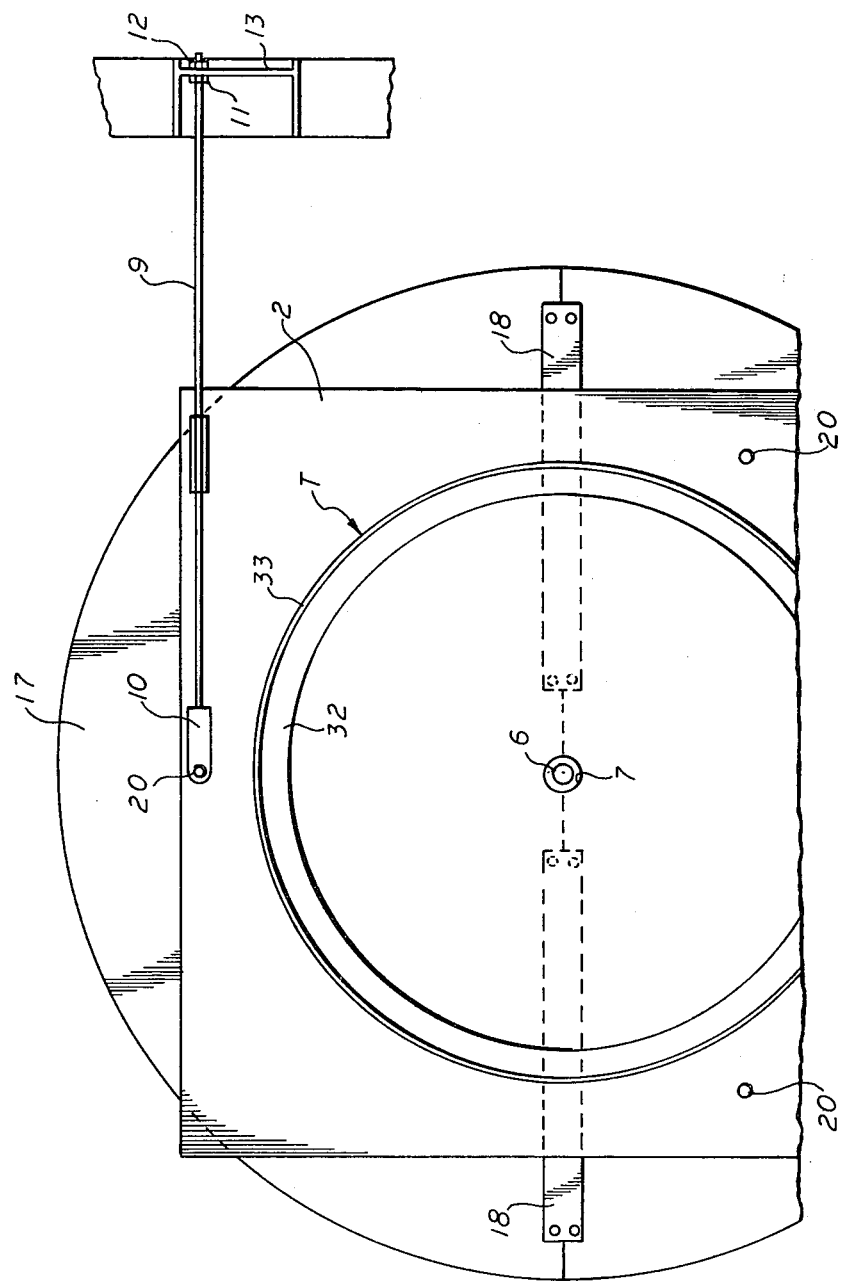
FIG. 2 is a quarter-section view of the test apparatus of the present invention, taken along lines 2—2 of FIG. 1.

The platen members 1 and 2 are supported from a fixed support assembly which may include a beam 3 attached to the floor 4. Attached to the beam 3 by flange 5, or the like, and extending upwardly therefrom is a threaded post member 6. It will be noted that the lower platen member is provided with a central aperture 7 through which the post member 6 passes. The lower end of the aperture 7 is tapered providing a bearing surface which rests on a corresponding bearing ridge surface 8a of a nut 8 which threadedly and rotatingly engages the threaded post 6. The bearing surfaces may be lubricated. Thus, the lower platen 2 is supported on the nut 8 which is rotatable relative thereto. To prevent rotation of the lower platen 2 upon rotation of the nut 8, a tie rod 9 may be connected to the periphery thereof by clevis 10, as best shown in FIG. 2. The opposite end of the tie rod 9 may be attached by nuts 11 and 12 to a fixed beam or post 13 adjacent to the test fixture. While the tie rod 9 prevents rotation, it does not prevent axial movement of lower platen 2.

Interposed between the upper platen 1 and the upper end of support post 6 is a load cell 14. The load cell 14 may actually be attached to the upper platen member by a bolt 15. The lower end of the load cell 14 is provided with a ball stud 16 which engages a corresponding pivot hole in the upper end of the threaded post 6. Thus, the entire weight of the upper platen and any additional weight which may be placed thereon are pivotally supported at the upper end of the threaded post 6.

As can be well understood, rotation of the nut 8 on the threaded post 6 will cause the lower platen 2 to move toward or away from the upper platen 1 depending upon the direction of rotation. To supply the force necessary for rotating the nut 8, a wheel 17, the periphery of which extends radially past the periphery of the lower platen 2, may be attached thereto. The wheel 17 may be made of plywood, and if desired, provided with metal stiffener strips 18. It will be noted that a space 19 exists between the wheel 17 and the lower platen 2 so that upon rotation of the nut 8 and wheel 17 there is no frictional engagement between the wheel 17 and lower platen 2, engagement of the lower platen 2 being only at the thrust bearing surface 8a of nut 8.

Located at spaced intervals about the periphery of the lower platen 2 is a plurality of limit devices which include rods 20, the lower ends of which are threaded for threaded engagement with corresponding threaded holes 21 in the lower platen 2. Bolts 22 may be threadedly inserted into corresponding threaded holes at the upper ends of the rods 20 so that the effective length of the limit device may be adjusted. Thus, the limit device is attached to the lower platen 2 and capable of engagement at the opposite end by the upper platen 1.

Although the test specimen T forms no part of the invention, the structure as illustrated in the drawings should be described. The specimen T may be formed by a series of longitudinally and helically disposed rods 30, 31 joined by welding at their intersections. The ends of the rods 30, 31 are attached to wooden rings 32. The circumference of the ends of the test specimen T may be potted in resin 33 to form parallel surfaces 34 through which test loads may be uniformly applied to the specimen T.

To test the specimen T, the specimen T is placed on the lower platen 2 with the upper platen 1 and attached load cell 14 removed. The upper platen 1 is then lowered by handling means, such as a crane, until the ball stud 16 on the load cell 14 rests in the hole at the upper end of threaded post 6. Miscellaneous weights such as shot bags may be used to balance the upper platen 1 about its central pivot point. The crane slings can then be removed or slacked. Since the entire weight of the platen 1 and any additional weights thereon rest on the load cell 14, the true weight can be recorded or monitored.

Next, the lower platen 2 and specimen T are raised by turning the wheel 17 until the specimen T contacts the upper platen 1. This point or position of contact can be determined by observing the load cell monitor (not shown). As the lower platen 2 and specimen T are raised, the specimen gradually lifts or flexes the upper platen 1 so that an increasing portion of the upper platen weight is transferred from the load cell 14 to the test specimen T. Loading a specimen in this fashion decreases the load cell reading. As the specimen T begins to fail or buckle, a reading can be taken to determine the buckling load.

As previously mentioned, a particularly significant feature of the test apparatus of the present invention is the means for limiting the movement of the lower platen 2 toward the upper platen 1. Before loading of the specimen T, the rods and bolts 20 and 22 are adjusted so that a predetermined gap exists between the ends of bolt 22 and the upper platen 1. After reaching the buckling point, the ends of the bolts 22 engage the upper platen 1 preventing further deformation of the specimen T. For example, in a test conducted with apparatus according to the present invention, a specimen was expected to fail at 2800 pounds with a prebuckling displacement of 0.020 inches. Each platen 1 and 2 was designed to deflect 0.010 inches at a cylindrical load of 2800 pounds. This would result in a postbuckle displacement in the specimen of 0.020 inches maximum. In order to lessen this displacement, it was necessary to use three limit devices 20, 22, placed symmetrically around the specimen. Prior to loading the specimen, the gaps between the ends of the bolts 22 and the upper platen 1 were set at 0.030 inches. Thus, the post-buckling displacement was reduced from 0.020 inches to 0.010 inches.

The compression test apparatus of the present invention is very simple in construction and operation. It is highly accurate and controllable. For example, six inches of rim displacement of the operating wheel for a particular test fixture results in 0.001 inch of total platen movement. Actual test experience demonstrates that an experienced operator can control the weight within ± two (2) pounds. A very important feature is the ability to stop a test instantaneously to prevent permanent damage to the test specimen.

While a single embodiment of the invention has been described, variations thereof can be made without departing from the spirit of the invention. Therefore, it is intended that the scope of the invention be limited only by the claims which follow.

I claim:

1. Apparatus for compressive testing of a test specimen comprising:
   vertically spaced upper and lower platen members between which a test specimen may be placed;
   fixed support means on which said platen members are supported, including a vertical post member;
   load indicator means interposed between said upper platen member and the upper end of the vertical post member of said support means through which the total weight of said upper platen member and any additional weight placed theron may be supported by said support means; and
   means for moving said lower platen member upwardly toward said upper platen member whereby an increasing portion of said total weight is transferred from said load indicator means to said test specimen.

2. Testing apparatus as set forth in claim 1 in which said lower platen member is provided with a central aperture through which said post member passes.

3. Testing apparatus as set forth in claim 2 in which said post member is threaded and in which said means for moving said lower platen upwardly comprises a nut member threadedly and rotatably engaging said threaded post member, said lower platen member resting on said nut member.

4. Testing apparatus as set forth in claim 3 in which said nut member is attached to operating means projecting beyond the periphery of said lower platen member and by which said nut member may be rotated for moving said lower platen upwardly.

5. Testing apparatus as set forth in claim 3 in which said nut member and said lower platen central aperture are provided with mutually engageable bearing surfaces permitting relative rotation between said nut member and said lower platen.

6. Testing apparatus as set forth in claim 5 in which said lower platen member is fixed against rotation relative to said post member.

7. Testing apparatus as set forth in claim 1 including limit means attached to one of said platen members and engageable with the other of said platen members, limiting movement of said lower platen member toward said upper platen member and to prevent permanent deformation of said test specimen.

8. Testing apparatus as set forth in claim 7 in which said limit means comprises a plurality of rods vertically disposed between said platen members near the peripheries thereof.

9. Testing apparatus as set forth in claim 8 in which one end of said rods is attached to said one platen member and the other end of said rods is provided with a vertically adjustable extension member for predetermining said limited movement of said lower platen member.

* * * * *